United States Patent [19]

Rosenblum

[11] 4,136,567

[45] Jan. 30, 1979

[54] PULP DENSITY METER

[75] Inventor: Frank Rosenblum, Ville Saint Laurent, Canada

[73] Assignee: Noranda Mines Limited, Toronto, Canada

[21] Appl. No.: 732,864

[22] Filed: Oct. 15, 1976

[30] Foreign Application Priority Data

Jul. 5, 1976 [CA] Canada .................................. 256295

[51] Int. Cl.² .............................................. G01N 9/26
[52] U.S. Cl. .................................................... 73/438
[58] Field of Search ...................... 73/438, 32 R, 299

[56] References Cited

U.S. PATENT DOCUMENTS

| 3,038,336 | 6/1962 | Peters | 73/438 |
| 3,360,995 | 1/1968 | Knauth | 73/438 |
| 3,399,573 | 9/1968 | Ponsar | 73/438 |
| 3,896,660 | 7/1975 | Valentyik | 73/438 |

FOREIGN PATENT DOCUMENTS

| 157554 | 1963 | U.S.S.R. | 73/438 |
| 274473 | 1970 | U.S.S.R. | 73/438 |

Primary Examiner—Stephen A. Kreitman
Attorney, Agent, or Firm—Fleit & Jacobson

[57] ABSTRACT

A device for measuring the density of a liquid or of a suspension of solids in a liquid comprises a holder of predetermined length, two pressure sensors mounted at one end of the holder and adapted to be submerged so that the two sensors are vertically at predetermined levels apart in the liquid, and a differential pressure transducer also mounted on the holder and coupled to the pressure sensors for providing an output voltage proportional to the pressure differential sensed by the pressure sensors.

6 Claims, 7 Drawing Figures

PULP DENSITY METER

This invention relates to a device for measuring the density of a liquid or of a suspension of solids in a liquid.

The density of any liquid or the percent solids in a liquid of known density have been generally measured up to now by manual monitoring devices. Continuous measuring devices such as gamma gauges have also been used. However, they are bulky and expensive to install. With the increasing acceptance of process control computers, there is an increasing trend towards the use of automatic sensors. It has been known for some time to derive the density of a liquid from the difference in pressure on two flexible diaphragms vertically spaced within such liquid. An apparatus for measuring the density of a liquid based on that principle has been disclosed in Canadian Pat. No. 450,332 granted Aug. 3, 1948. However, this apparatus was permanently mounted on the wall of the tank containing the liquid the density of which was to be measured. In addition, the pressure differential was detected by a complex mechanism including a mercury column.

It is the object of the present invention to provide a density measuring device which is portable, simple, accurate and does not require any additional interface other than an optional electrical amplifier when used with a recorder or controller.

The density measuring device, in accordance with the invention, comprises a holder of predetermined length, two pressure sensors mounted at one end of the holder and adapted to be submerged in the liquid so that the two sensors are vertically at predetermined levels apart, and a differential pressure transducer for providing an output voltage proportional to the pressure differential sensed by the pressure sensors.

The holder is preferably adapted to be placed vertically in the liquid and the two pressure sensors mounted a predetermined distance apart one above the other at one end of the holder. The differential pressure transducer may be contained in an enclosure mounted at the other end of the holder although it could be placed anywhere on the holder.

The pressure sensors and at least the portion of the holder which is submerged in the liquid are preferably made of corrosion and abrasion resistant material so as to resist adverse working conditions.

The pressure sensors are diaphragm type sensors. The differential pressure transducers may be variable reluctance units, variable capacitance units, or differential transformer type units although strain gauges and piezoelectric devices can also be used. Such differential pressure transducers should have a low volume and a low displacement so as to provide better accuracy. There are a number of commercial transducers capable of providing a suitable output voltage for differential pressures of one psid or less. In general, the whole assembly including the pressure sensors and the differential pressure transducer should have a low volume so as to reduce the diaphragm movement with change of pressure.

The enclosure containing the differential pressure transducer is preferably made of a bottom plate and an inverted cup housing secured to such plate. A bracket is mounted on the bottom plate and the pressure transducer is mounted on the bracket. In addition, an annular slot is preferably provided in the bottom plate and an O-ring is located in such slot for sealing the enclosure when the housing is secured to the bottom plate.

The invention will now be disclosed, by way of example, with reference to the accompanying drawings in which.

Figure 1:
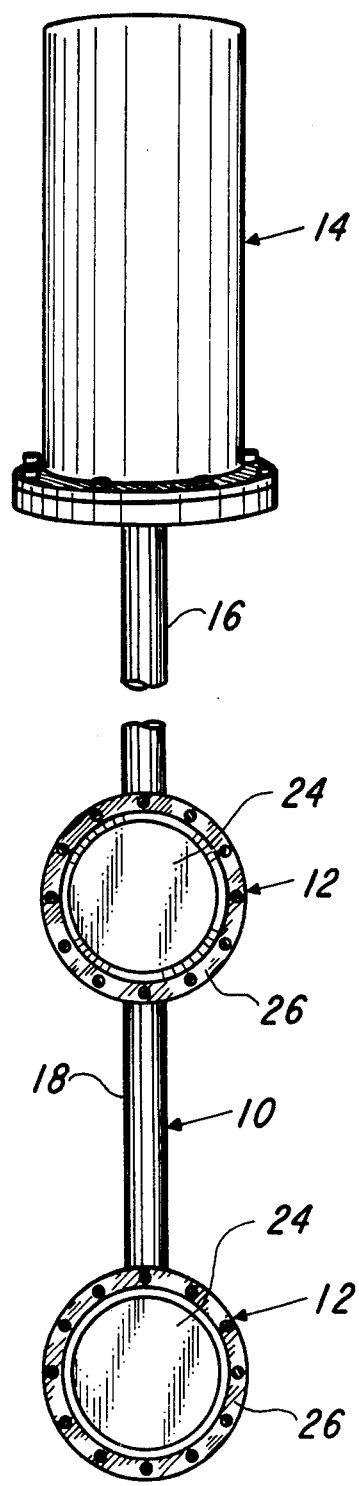
FIG. 1 illustrates an embodiment of a density measuring device in accordance with the invention.
Figure 2:
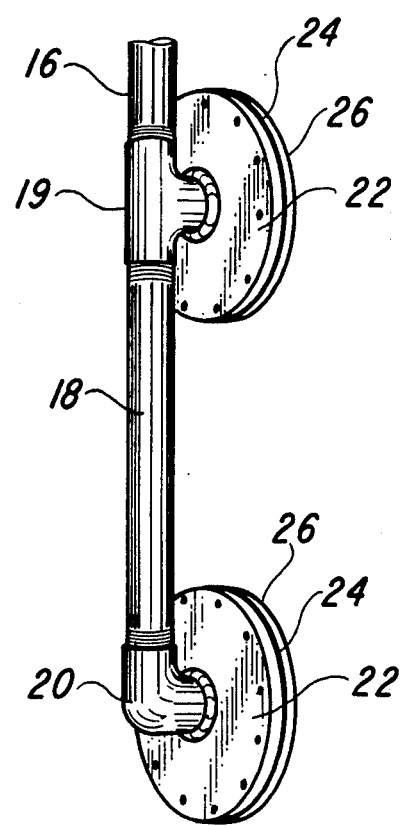
FIG. 2 illustrates a side view of the lower part of the density measuring device showing details of the assembly of the pressure sensors.
Figure 3:
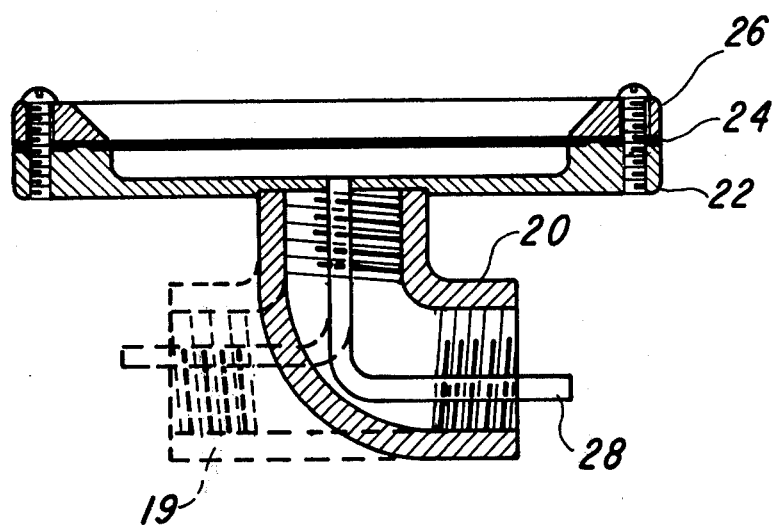
FIG. 3 illustrates a section view taken through the pressure sensors.

Referring to FIG. 1, the density measuring device generally comprises a holder 10, two pressure sensors 12 mounted a predetermined distance apart at one end of the holder and an enclosure 14 mounted at the other end of the holder. The holder is preferably made of stainless steel or other corrosion and abrasion resistant material so as to permit the use of the density measuring device in corrosive and abrasive solutions. As more clearly seen in FIG. 2, the holder is made of two stainless steel pipe sections 16 and 18 joined by a stainless steel T fitting 19 upon which is secured a first pressure sensor. The other pressure sensor is secured to a stainless steel elbow 20 which is threaded into the other end of stainless steel pipe 18. As illustrated in FIG. 3, the two pressure sensors each consist of a shallow housing 22 which is closed by a diaphragm 24 itself secured to the housing 22 by an annular ring 26. The housing 22 of each pressure sensor has a hole at the bottom to which is welded the end of a tube 28 which extends through the center of the holder up to a differential pressure transducer located in enclosure 14 as it will be disclosed in detail later. Although air is normally used to couple the pressure sensors and the differential pressure transducer, it will be understood that liquids could also be used.

Figure 4A:
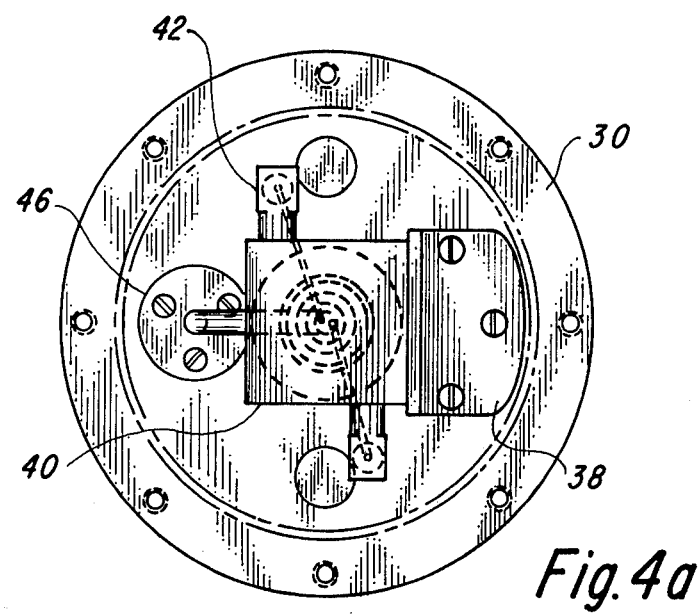
FIGS. 4a and 4b illustrate details of the enclosure in which is housed the differential pressure transducer.
Figure 4B:
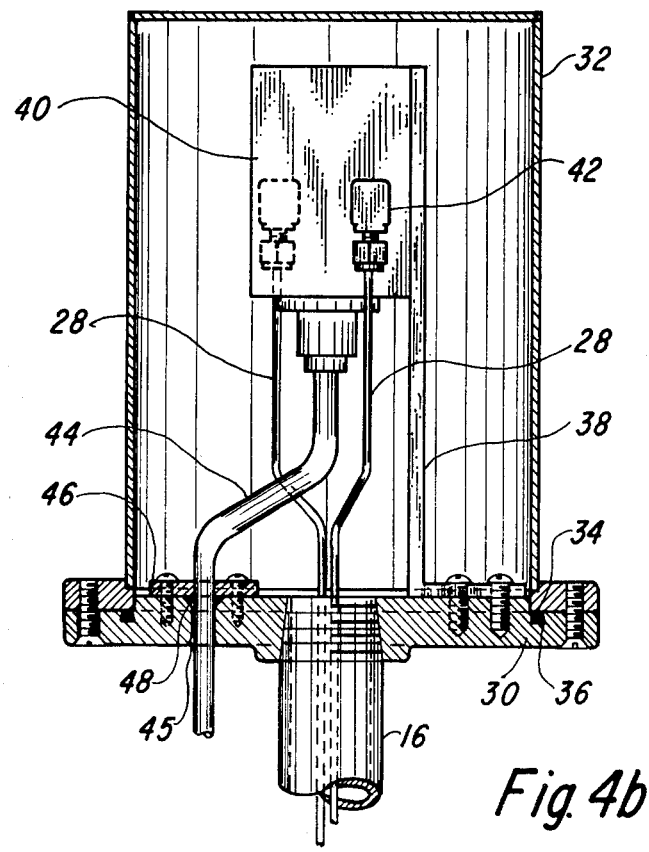

As illustrated more clearly in FIGS. 4a and 4b, the enclosure 14 consists of a bottom plate 30 which is threaded or otherwise secured to the end of pipe 16 and of an inverted cup housing 32 which is secured to bottom plate 30. An O-ring 34 is placed in an annular slot 36 in the bottom plate 30 for sealing enclosure 14 when the housing 32 is secured to bottom plate 30. This permits the use of the density measuring device in adverse working conditions.

A bracket 38 is secured to bottom plate 30 and a differential pressure transducer 40 is attached to the bracket. Various pressure transducers are available depending on the pressure differential to be measured. Examples of suitable transducers are the Celesco P7D variable reluctance pressure transducer, the Setra Model 227 variable capacitance transducer, or the Hewlett Packard differential transformer model 270. Strain gauges and piezoelectric devices could also be used. The differential pressure sensed by the pressure sensors is fed to inputs 42 of the transducer through tubes 28. The output of the transducer is fed through cable 44. The transducer normally requires a low voltage input for operation. This voltage is provided by a suitable supply which may be located in the enclosure 14, or may be fed through cable 44. Cable 44 protrudes through a hole 45 in the base plate 30 and is secured to the base plate by a connector 46. The hole 45 is sealed by O-ring 48.

The output of transducer 40 may require amplification before being fed to a recorder or a controller.

The distance between the two pressure sensors depends upon the sensitivity of the differential pressure transducer and upon the density or specific gravity to be measured. For example, with the above mentioned Selesco P7D transducer which is capable of measuring a pressure differential of 1 psid, a distance of 11 inches between the pressure sensors has been found satisfactory for measuring liquid densities up to 2 kgms/liter as it provides a reading of slightly less than half its full output voltage when measuring the density of water (27.68 inches of water = 1 psi). With a Setra Model 227 transducer, which is capable of measuring a pressure differential of 0.5 psid, a distance of 5 inches between pressure sensors has been found adequate. Hewlett Packard Model 270 is capable of measuring a pressure differential of 40 cm of water and has been found to operate satisfactorily with a spacing of 8 inches between the two pressure sensors.

Figure 5:
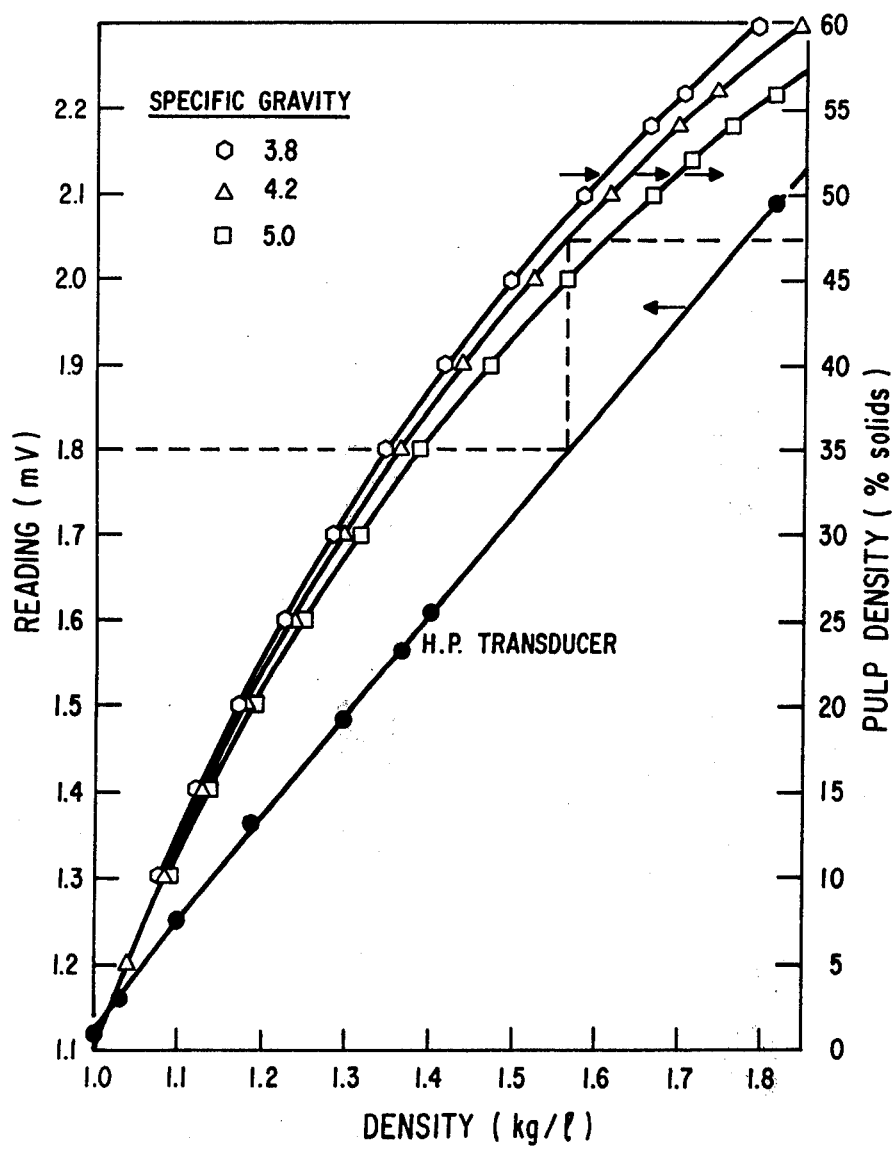
FIG. 5 illustrates the voltage density characteristic of a differential pressure transducer.

FIG. 5 illustrates a graph of the output voltage obtained with a Hewlett Packard Model 270 transducer when used in the device in accordance with the invention to check the density of liquids of known densities. FIG. 5 also shows the theoritical curves illustrating the pulp density (percent solids in liquid) versus density of the solution for solids of various specific gravities. From FIG. 5, one will read that an output voltage of 1.8 mv on the Hewlett Packard Model 270 transducer gives a reading of 47% solids in solution with a solid having a specific gravity of 4.2. It will be easily understood that a reading instrument can be calibrated accordingly or tables made which would provide the % solids directly from the output voltage of the transducer for liquids containing solids of various specific gravities in solution.

Figure 6:
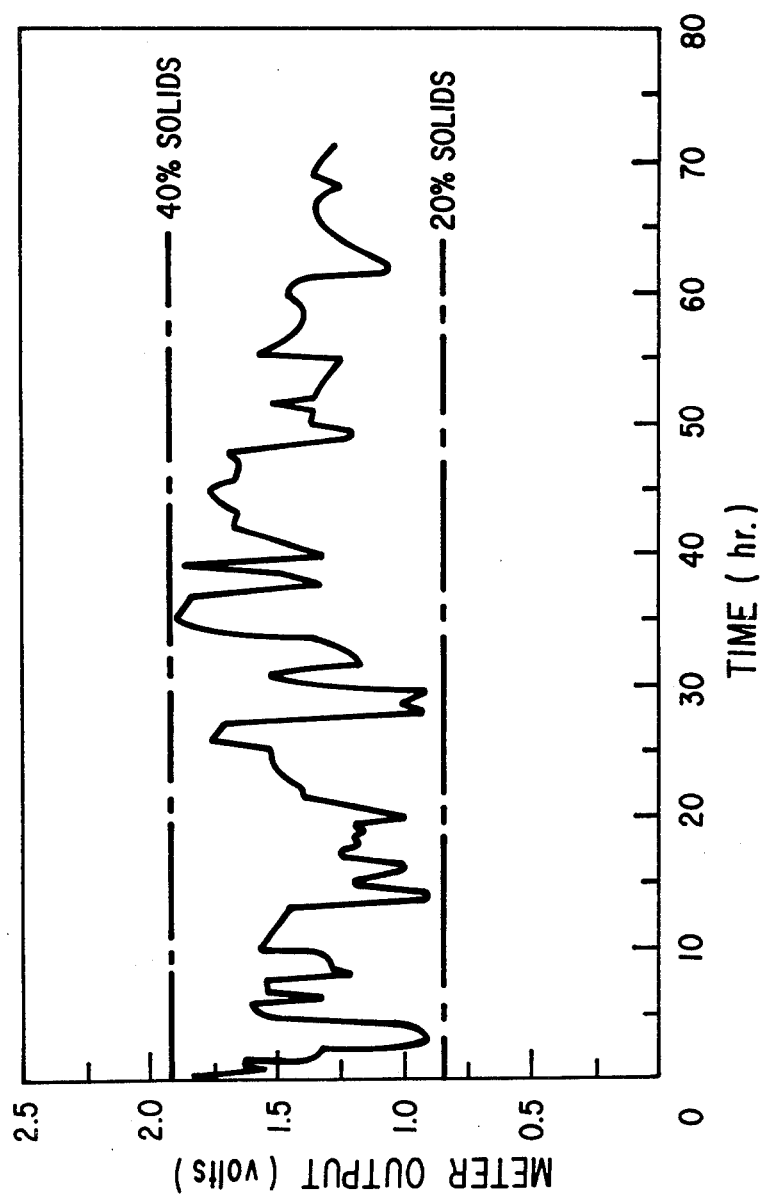
FIG. 6 illustrates a pulp density recording made with the density measuring device in accordance with the invention.

The device in accordance with the invention was tested in a lead dezincing circuit conditioner at Brunswick Mining and Smelting Corporation Limited. The pulp density in such conditioner is normally adjusted manually by water addition to the feed pump and control of the density is difficult and varies widely. The two pressure sensors were immersed about one foot (top pressure sensor) in the pulp. A record of the meter output for the test over a period of 72 hours is shown in FIG. 6. The density, checked from time to time with a Marcy balance, was found to vary in the range 20–40% solids. Although an acurate calibration was not carried out, the nearly linear response of the density measuring device in accordance with the invention to change in density over this range was demonstrated. The output is a true linear function of the specific gravity of the pulp. The smaller variability in the pulp density after about 50 hours of density measuring device operation is due to the availability of the pulp density data to the operators resulting in improved control of the water addition. Automatic control of the water addition could easily be implemented from the output of the density measuring device. Optimization of flotation reagent addition at constant pulp density would then be possible.

It will be noted that the meter output reading is the transducer output compensated for 0 reading (−1.12 mv as seen in FIG. 5) and amplified by a factor of about 3800.

Although the invention has been disclosed with reference to a preferred embodiment thereof, it is to be understood that various modifications may be made thereto within the scope of the following claims.

What is claimed is:

1. A portable device adapted for insertion into a body of liquid for measuring the density of said liquid or of a suspension of solids in said liquid comprising:
   (a) a hollow holder of predetermined length;
   (b) two gas-tight diaphragm type pressure sensors mounted a predetermined distance apart one above the other at one end of the holder and adapted to be submerged in the liquid so that the two sensors are vertically at predetermined levels apart;
   (c) a gas-tight differential pressure transducer mounted on the holder at the end opposite from said pressure sensors;
   (d) tubes extending through the center of said holder and connecting the two pressure sensors to the differential pressure transducer to form a closed gas circuit therebetween, said differential pressure transducer providing an output voltage proportional to the pressure differential sensed by the pressure sensors;
   (e) a medium in said closed gas circuit for coupling the two pressure sensors to the differential pressure transducer, said medium being a gas; and
   (f) an enclosure for containing said differential pressure transducer.

2. A device as defined in claim 1, wherein the pressure sensors and at least the portion of the holder which is submerged in the liquid are made of corrosion and abrasion resistant material.

3. A device as defined in claim 1, wherein the enclosure is made of a bottom plate and an inverted cup housing secured to such bottom plate.

4. A device as defined in claim 3, further comprising a bracket secured to said bottom plate and wherein said pressure transducer is mounted on said bracket.

5. A device as defined in claim 3, wherein an annular slot is located in said bottom plate and further comprising an O-ring located in said slot for sealing the enclosure when said housing is secured to said bottom plate.

6. A device as claimed in claim 1, wherein the device including the two pressure sensors and the differential pressure transducer is of low volume thereby requiring a low volume displacement of the coupling medium.

* * * * *